United States Patent [19]

Kato et al.

[11] Patent Number: 4,528,086
[45] Date of Patent: Jul. 9, 1985

[54] OXYGEN SENSOR WITH HEATER

[75] Inventors: Nobuhide Kato, Aichi; Takao Murase, Konan, both of Japan

[73] Assignee: NGK Insulators, Ltd., Japan

[21] Appl. No.: 604,474

[22] Filed: Apr. 27, 1984

[30] Foreign Application Priority Data

May 9, 1983 [JP] Japan ............................ 58-68665[U]

[51] Int. Cl.³ ............................................. G01N 27/46
[52] U.S. Cl. .................................... 204/427; 204/429; 219/541
[58] Field of Search ................. 204/427, 428, 429, 1 S, 204/424–426, 408, 412; 73/23; 219/553, 541; 123/489

[56] References Cited

U.S. PATENT DOCUMENTS 4,339,320  7/1982  Friese et al. ........................ 204/408
4,383,906  5/1983  Sano et al. ....................... 204/424 X Primary Examiner—David Simmons
Attorney, Agent, or Firm—Parkhurst & Oliff

[57] ABSTRACT

An oxygen sensor having a bar-shaped heater inserted in an elongate bore formed in a tubular body of solid electrolyte which has porous platinum electrodes on its inner and outer surfaces and which is supported by a housing such that its closed end portion is exposed to exhaust gas and such that the elongate bore is gas-tight with respect to the exhaust gas. The bar-shaped heater comprises a heating resistor having a positive temperature coefficient, a ceramic body carrying the heating resistor so as to embed the latter, and a pair of lead wires. The ceramic body has on its periphery a pair of terminal pads connected to the heating resistor. The ends of the lead wires are brazed to the terminal pads with a brazing material containing silver. The ceramic body further has a pair of equipotential members disposed outwardly of the pair of terminal pads to enclose at least portions of the peripheries of the pads which are opposite to each other.

5 Claims, 7 Drawing Figures

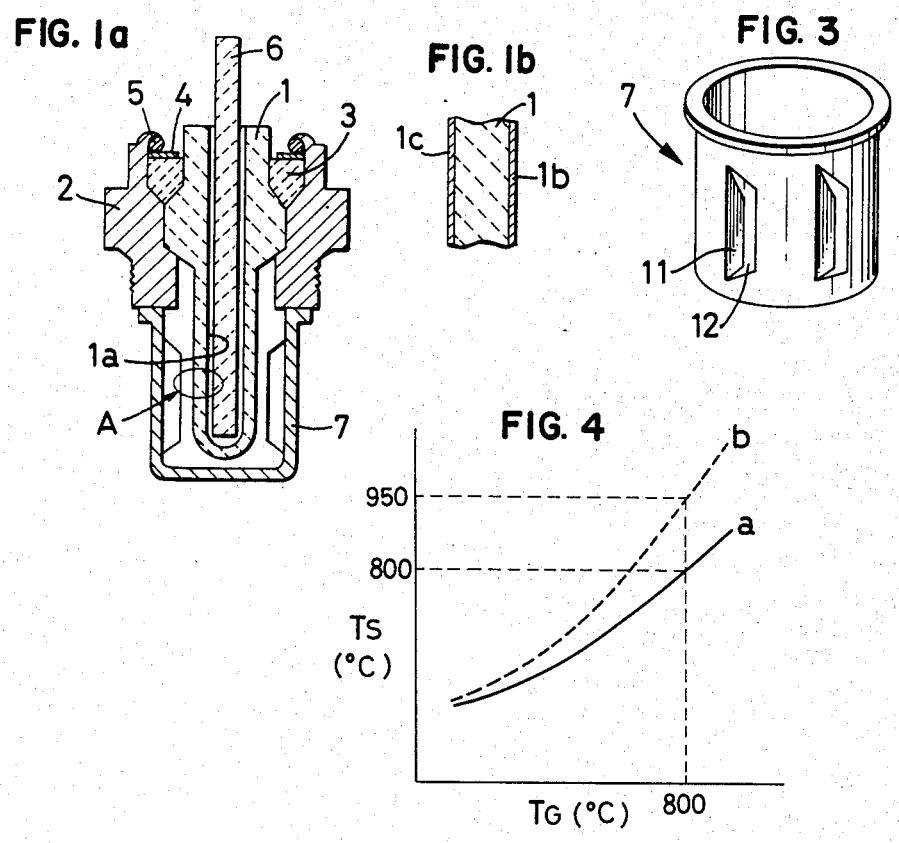
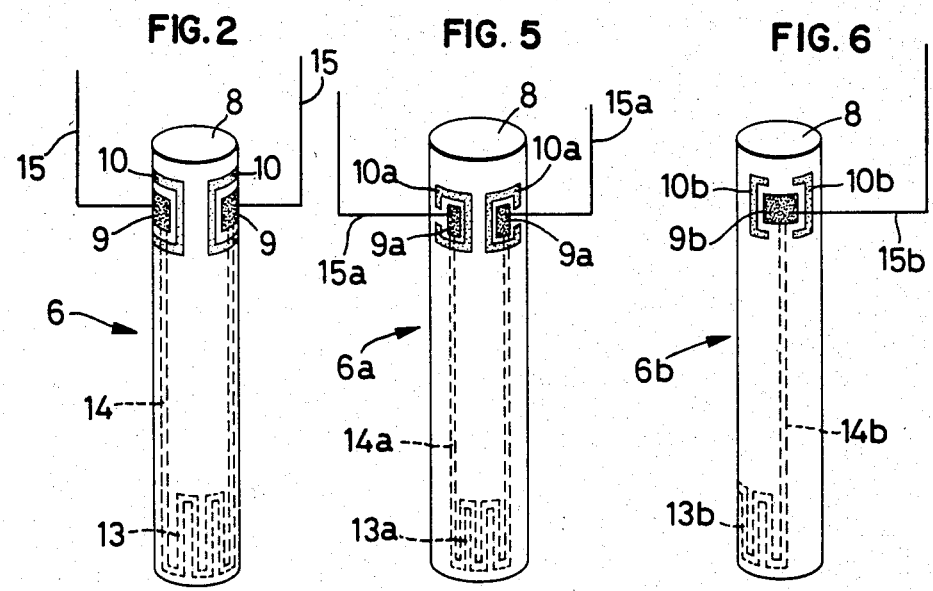

OXYGEN SENSOR WITH HEATER

BACKGROUND OF THE INVENTION

The present invention relates generally to an oxygen sensor for detecting concentration of oxygen contained in exhaust gas emitted from an internal combustion engine. More particularly, the invention is concerned with such an oxygen sensor having a bar-shaped heater disposed in an elongate bore formed in a tubular body of solid electrolyte.

In the art of controlling an air-fuel (A/F) ratio of an internal combustion engine for an automotive vehicle or for other applications, it is known to use an oxygen sensor which employs a mass of zirconia or other solid oxygen-ion conductive electrolyte to detect a content or concentration of oxygen in exhaust gas produced by the engine, according to the principle of an oxygen concentration cell. For example, such an oxygen sensor uses a solid electrolyte body of zirconia which is provided on its inner and outer surfaces with porous platinum electrodes, respectively. The electrode on the inner surface which defines an inner elongate bore in the zirconia body, is exposed to an ambient atmosphere and serves as a reference electrode (anode) which is exposed to a reference gas whose oxygen concentration is known. On the other hand, the electrode provided on the outer surface of the zirconia body is exposed to exhaust gas to be measured, so that this electrode serves as a measuring (cathode) electrode to monitor oxygen content of the exhaust gas. This oxygen sensor measures the oxygen concentration in the exhaust gas by measuring an electromotive force which is induced in response to a difference in the oxygen concentration between the reference and measuring electrodes.

However, the induced electromotive force is unstable until the solid electrolyte has been heated to a given point. Thus, the above type of oxygen sensor suffers a drawback that it is incapable of effecting an accurate control of an air-fuel ratio of the engine while the temperature of the exhaust gas of the engine is relatively low, for example while the engine is idling or immediately after the engine is started in its cold condition.

To solve such a drawback experienced in the art, it has been proposed to positively heat a solid electrolyte body by inserting a heater into an elongate cylindrical hole formed in the electrolyte body. For instance, Japanese Patent application laid open in 1979 under Japanese Publication No. 54-13396 discloses a heater which consists of an insulator bar and a heating wire (resistance wire) wound on the surface of the insulator bar. Further, Japanese Patent application laid open in the same year under Japanese Publication No. 54-22894 shows a so-called sheathed heater which uses a resistance coil wire disposed in a metal sleeve which is filled with a powdered electrically insulating material of high thermal conductivity so as to secure the coil wire in the metal sleeve.

Such proposed oxygen sensors equipped with a heater are disadvantageous in that their solid electrolyte is susceptible to excessive heat when the temperature of the exhaust gas of an internal combustion engine is elevated, whereby the porous platinum electrodes tend to be sintered with a result of reducing a rate of reaction of the measuring electrode to the exhaust gas, or a spinel coating layer protecting the electrodes tends to crack or flake off. Further, the heater is subject to an excessively high temperature due to a combined effect of its self-heating and exposure to heat of the exhaust gas, thereby suffering breakage of its inner resistance wire.

On the other hand, an effort to restrain heat generation of the heater to minimize such disadvantages as indicated above, will create another incovenience of insufficient heating of the solid electrolyte while the exhaust gas is low in temperature, or undesired requirement of extra time for heating the solid electrolyte after the start of the engine, before the electromotive force induced by the sensor reaches a level for accurate detection of the oxygen concentration.

The above inconvenience of insufficient heating of the solid electrolyte is serious particularly when a battery voltage to actuate the heater is low, that is, immediately after the engine is started or while the engine is operated in a cold state. On the contrary, when the battery voltage rises with the engine speed, the temperature of the exhaust gas is elevated. This will aggravate the previously indicated drawback of excessive heating of the solid electrolyte.

Further, a heater used in the traditional oxygen sensor suffers a problem of migration of silver which is used as one component of a brazing material for connecting lead wires to electric terminals of the heater. More particularly, the silver ions migrate or move from one of the electric terminals to the other, under the influence of electric field during a long period of power application to the heater. This migration phenomenon of silver causes short-circuiting of the electric terminals.

SUMMARY OF THE INVENTION

It is accordingly an object of the present invention to provide an oxygen sensor having an improved heater inserted in an elongate bore formed in a body of solid electrolyte, which is durable and reliable in operation even in comparatively varying environmental conditions, and which is substantially free from a problem of migration of a brazing material used to connect lead wires to the heater.

According to the present invention, there is provided an oxygen sensor comprising: a tubular body of solid electrolyte having an elongate bore which is closed at one end of the tubular body and open at the other end, and further having reference and measuring electrodes on inner and outer surfaces thereof, respectively; a housing which supports or retains the body of solid electrolyte such that the outer surface of the latter is exposed at the closed end to exhaust gas, and such that the elongate bore in the tubular body of solid electrolyte is held in gas-tight condition with respect to the exhaust gas; and a bar-shaped heater inserted in the elongate bore in the tubular electrolyte body. The bar-shaped heater comprises a heating resistor having a positive temperature coefficient, a ceramic body carrying the heating resistor so as to embed the heating resistor, and a pair of lead wires for connecting the heating resistor to an electric power source. The ceramic body has, on its outer peripheral surface a pair of terminal pads connected to the heating resistor. At the end portion, each of the lead wires is brazed to be connected to corresponding one of the terminal pads with a brazing material containing silver as one of its components. The ceramic body further has on the outer peripheral surface a pair of equipotential members disposed outwardly of the pair of terminal pads, respectively. These equipotential members enclose at least portions of the peripheries of the corresponding terminal pads which are opposite to each other.

In the oxygen sensor constructed as described above wherein the heating resistor embedded in the ceramic body has a positive temperature coefficient, the heater provides a relatively large amount of heat when the temperature of the exhaust gas is comparatively low, but provides a relatively small amount of heat when the exhaust gas temperature is comparatively high, whereby the solid electrolyte is heated to a sufficient level within a short length of time after the start of elevation of the exhaust gas, and the solid electrolyte and the heating resistor are less likely to be overheated even when the sensor is exposed to the exhaust gas of high temperature. A further advantage of the instant oxygen sensor is provided by the equipotential members which are disposed outwardly of the corresponding pair of electric terminal pads, such that the equipotential members enclose at least portions of the terminal pads which are opposite to each other. These equipotential members serve to prevent otherwise possible migration of the silver content of the brazing material from one of the terminal pads toward the other under the influence of electromotive force, thereby avoiding consequent short-circuiting between the terminal pads, or cracking of the brazing material due to decrease in its mass caused by the silver migration. With the above arrangements, the oxygen sensor according to the invention is capable of providing reliable electrical outputs accurately representing oxygen concentration of an exhaust gas from an internal combustion engine, and therefore capable of controlling an air-fuel ratio of the engine with high precision and for a prolonged period of service.

According to one preferred aspect of the invention, each of the equipotential members comprises a pattern of band enclosing said portions of the corresponding terminal pad, a width of the band being not less than 0.1 mm.

In accordance with an advantageous form of the invention, the above pattern of band is spaced from the outer periphery of the corresponding terminal pad. Preferably, an area of a space between the pattern of band and the terminal pad is held not more than one half of a surface area of the corresponding terminal pad.

According to a further advantageous aspect of the invention, the temperature coefficient of the heating resistor is not less than 0.3%/° C., so that the principle of the invention is practiced more effectively.

BRIEF DESCRIPTION OF THE DRAWING

The above and other objects, features and advantages of the present invention will be better understood from reading the following description of the preferred embodiments taken in conjunction with the accompanying drawing in which:

FIG. 1(a) is an elevational view in cross section of one embodiment of an oxygen sensor with a heater of the present invention;

FIG. 1(b) is an enlarged fragmentary view in cross section of a portion A of a tubular body of solid electrolyte of the oxygen sensor of FIG. 1(a);

FIG. 2 is a schematic illustration of one form of the bar-shaped heater used in the oxygen sensor of FIG. 1(a);

FIG. 3 is a perspective view of one form of a protective metal tube used in the oxygen sensor of FIG. 1(a);

FIG. 4 is a graphical representation of a solid electrolyte temperature in relation to an exhaust gas temperature in the oxygen sensor of the invention, as compared with that in an oxygen sensor known in the art; and FIGS. 5 and 6 are schematic illustrations, showing alternative forms of the bar-shaped heater used according to the invention in place of the heater of FIG. 2.

DETAILED DESCRIPTION OF THE PREFERRED EMBODIMENTS

Referring first to FIGS. 1-4, there is illustrated a preferred form of an oxygen sensor embodying the present invention, wherein a tubular body 1 of solid electrolyte such as zirconia is supported by a housing 2. The tubular body 1 has an elongate cylindrical bore 1a which is formed longitudinally of the body 1. The elongate bore 1a is closed at one end of the body 1 which is exposed to exhaust gas emitted through an exhaust conduit (not shown), for example, from an internal combustion engine of an automotive vehicle. The elongate body 1a is open, at the other end of the tubular body, to ambient atmosphere used as a reference gas. The tubular solid electrolyte body 1 is provided at its inner and outer surfaces with a reference electrode 1b (anode) and a measuring electrode 1c (cathode), respectively, as shown in FIG. 1(b), both electrodes 1b and 1c being made of porous platinum (Pt). The tubular body 1 is retained and sealed in the housing 2, via a talc 3, a metal washer 4 and a metal ring 5, such that the elongate bore 1a is held in gas-tight condition with respect to the exhaust gas, i.e., so that the ambient atmosphere (air) and the exhaust gas do not meet with each other. In the elongate bore 1a, there is inserted a bar-shaped heater 6 to heat the solid electrolyte of the tubular body 1. The closed end portion of the tubular body 1 is enclosed by a protective metal tube 7, which protects the closed end portion against direct exposure thereof to a stream, of the exhaust gas flowing through the exhaust conduit. The protective metal tube 7 is fixed at its upper end to the lower end of the housing 2, and has flute openings 12 in its peripheral wall to introduce the exhaust gas into the interior of the tube 7 for exposure of the lower or closed end portion of the electrolyte body 1 to the exhaust gas. These flute openings 12 are formed by cutting parts of the peripheral wall and bending these cut parts radially inwardly of the protective metal tube 7 so as to form louver plates 11, as illustrated in FIG. 3.

The bar-shaped heater 6 inserted in the elongate bore 1a of the tubular solid electrolyte body 1 as shown in FIG. 1(a), comprises a ceramic body 8 made of ceramics such as alumina, as shown in FIG. 2. The ceramic body 8 carries a heating resistor in the form of a printed heating portion 13, such that the heating resistor is embedded in the mass of the ceramic body 8. The heating portion 13 is connected to a pair of printed lead portions 14 which are connected to a corresponding pair of terminal pads 9. The heating portion 13 and the lead portions 14 are respectively imprints of electrically resistant and conductive materials which are applied in a paste state to the surface of a ceramic bar to form a predetermined printed pattern, as shown in broken lines in FIG. 2. The ceramic bar with the heating and lead portions 13 and 14 is covered with a ceramic layer to constitute the ceramic body 8. The ends of the lead portions 14 not connected to the heating portion 13 penetrate the ceramic layer to reach the outer peripheral surface of the ceramic body 8, so that the lead portions 14 are connected to the terminal pads 9. The lead portions 14 are connected to an electric power source through a corresponding pair of lead wires 15, 15. Each lead wire 9' is brazed at its one end to corresponding one of the pair of terminal pads 9 which are disposed at diametrically opposite positions on the outer peripheral surface of the bar-shaped ceramic body 8. More specifically, the terminal pads 9 are disposed along parts of the peripheral surface of the ceramic body 8, such that they are electrically connected to the lead portions 14 and consequently to the heating portions 13. The end portions of the lead wires 15 and the corresponding terminal pads 9 are brazed together by applying a suitable brazing material containing Ag (silver) as one of its components. Outwardly of the pair of terminal pads 9, there are disposed a corresponding pair of equipotential members 10, which are patterns of band enclosing the entire peripheries of the pair of terminal pads 9. The equipotential members 10 have the same potential at all points in their pattern of band, and are made of a heat-resistant metal such as nickel and tungsten.

The heating portion 13 used as the heating resistor in the bar-shaped ceramic heater 6 has a positive temperature coefficient of 0.5%/° C. With this selection of the temperature coefficient, the resistance of the heating resistor (heating portion 13) is increased and its amount of heat generation is decreased as the temperature of the exhaust gas is elevated, whereby otherwise possible overheating of the solid electrolyte 1 and the heater 6 is prevented at the elevated temperature of the exhaust gas. On the other hand, when the exhaust gas temperature is relatively low, the resistance of the heating resistor 13 is held low and its amount of heat generation is increased, thereby making it possible to raise the temperature of the solid electrolyte 1 to a level at which an accurate electromotive force is induced by the electrodes $1b$, $1c$, in a comparatively short time after the start of the vehicle engine in its cold state, or making it possible to heat the solid electrolyte 1 sufficiently while the engine is idling.

A graph of FIG. 4 shows a temperature $T_S$ (° C.) of the solid electrolyte 1 in relation to a temperature $T_G$ (° C.) of the exhaust gas, wherein a curve (a) represents the relation between the temperatures $T_S$ and $T_G$ obtained on the ceramic heater of the instant oxygen sensor, and a curve (b) represents the same relation obtained on a known sheathed heater employing a nichrome wire which is selected so that a length of time from the start of a cold engine to generation of an electromotive force from a sensor using the sheathed heater is substantially equal to that of the oxygen sensor of the invention. At the exhaust temperature of 800° C., the temperature of the solid electrolyte 1 heated by the ceramic heater 6 of the invention is 800° C. as shown by the curve (a), while the temperature of a solid electrolyte heated by the known sheathed heater is 950° C. as indicated by the curve (b). This graph indicates less heating of the electrolyte by the cemramic heater 6 and consequently reduced chance of overheating of the electrolyte when the exhaust temperature $T_G$ is relatively high.

Experiments were conducted, on the oxygen sensor of the invention and the known oxygen sensor used in the measurements of FIG. 4, to check for outlook or appearance of the solid electrolytes and physical condition of the heaters after these sensors are placed in continuous service for 300 hours at an exhaust gas temperature of 800° C. The results on the known sensor showed some cracks of a spinel coating layer which is applied to the outer surface of the solid electrolyte body, and 70% breakage of resistance wire of the sheathed heater. On the oxygen sensor of the invention, neither such cracks nor such breakage were found.

As indicated above, the ceramic heater 6 using the printed heating portion 13 having a positive temperature coefficient, has a relatively low level of resistance of the heating element at low exhaust temperatures, and consequently an increased amount of heat generation from the heater, thereby allowing a rapid heating of the solid electrolyte and consequently an earlier generation of an electromotive force from the sensor. This advantage is obtained, for example, immediately after the start of an cold engine, or when the engine is running at its idling speed. On the contrary, a rise of the exhaust temperature to a considerably higher level will cause an appreciable increase in the resistance of the heating portion 13. For example, the resistance at 800° C. is approximately five times as high as that at the room temperature. Thus, the possibility of overheating of the solid electrolyte body 1 and the heater 6 is minimized. It is noted that a positive temperature coefficient of the heating portion 13 is important to the heat regulating or controlling performance of the heater 6 as discussed above. In the case where the oxygen sensor is used for an internal combustion engine, it is preferred that the temperature coefficient of the heating resistor 13 be held not less than 0.3%/° C. This coefficient which should be a positive value, is determined by kinds of electrically resistant metal powders selected for the heating resistor 13, and by an amount of glass frits contained in the paste of such metal powders.

In a common oxygen sensor, an Ag-Cu-Zn eutectic hard solder or a brazing material containing Ag one of its components is widely used to connect lead wires to electric terminals of a bar-shaped heater. It is recognized in the art that the Ag content of the solder or brazing material migrates between the electric terminals, and the migration may cause short-circuiting of the terminals or cracking at these electrical connections on the heater. This migration of silver is a phenomenon wherein Ag ions produced through ionization of AgOH or $Ag_2O$ will drift or move, under the influence of electric field, towards one or the other electric terminal.

In the light of the above phenomenon, the instant ceramic heater 6 employs the equipotential members 10 enclosing the respective terminal pads 9. In operation of the heater 6, the silver ions moving from one of the pads 9 to the other reach the inner periphery of the equipotential member 10 corresponding to said one pad 9. However, the silver ions do not pass across the width of band of the equipotental member 10 toward the outer periphery thereof, because no electric field to cause migration of the silver ions exists within the band of the equipotential member 10. As a result, the migration of silver ions terminates at the inner periphery of the equipotential member 10. Thus, the equipotential members 10 protect the terminal pads 9 against their short-circuiting due to migration of the silver contained in the brazing materials applied to fix the lead wires 15 to the terminal pads 9.

As suggested by the above description, the effect of the equipotential members 10 to prevent the silver migration between the two terminal pads 9, is increased as the width of the equipotential band 10 is increased. In this respect, it is preferred that the width of the band 10 be not less than 0.5 mm. However, the intended result according to the invention may be obtained as long as the width of the band 10 is not less than 0.1 mm.

As illustrated in FIG. 2, the equipotential members 10 are disposed such that their inner periphery is spaced from the outer periphery of the corresponding terminal pads 9. It is recognized, however, that the silver ion migration and the resultant decrease in the mass of the brazing material are reduced as the gap between the equipotential band 10 and the terminal pad 9 is decreased. Therefore, from the standpoint of preventing the cracking of the brazing material due to the silver ion migration, it is advantageous to dispose the equipotential members 10 as close to the terminal pads 9 as possible. Generally, it is appreciated to determine the gap between the band 10 and the terminal pad 9 such that an area of a space between the two is held not more than one half of a surface area of the terminal pad 9.

While it is preferred that the equipotential members used according to the invention be designed to enclose the entire periphery of the terminal pads 9, a pattern of band of the equipotential member may be designed as shown in FIGS. 5 and 6. More specifically described, a ceramic heater 6a of FIG. 5 carries a pair of terminal pads 9a which are disposed on the same circumferential half of the ceramic body 8, unlike the terminal pads 9 of FIG. 2 which are located opposite to each other diametrically of the ceramic body 8. Outwardly of these pads 9a are disposed a corresponding pair of equipotential members 10a which are C-shaped patterns of band enclosing the outer peripheries of the terminal pads 9a except the portions which are not opposite to each other. In other words, the C-shaped bands 10a enclose the portions of the peripheries of the pads 9a which are opposite to each other circumferentially of the ceramic body 8. In a ceramic heater 6b of FIG. 6, each of terminal pads 9b is partially enclosed by two equipotential members 10b which are patterns of band similar to square brackets. These equipotential members 10b are disposed to sandwitch the terminal pad 9b such that the latter is not enclosed at its upper and lower sides as viewed in FIG. 6. In conclusion, the equipotential members used according to the invention do not necessarily enclose the entire outer periphery of the respective terminal pads. That is, the equipotential members may be open at the portions of the terminal pads which are not opposite to each other, because the magnitude of an electric field is considerably lower at these portions than at the opposite portions. Thus, the patterns of band of the equipotential members may be designed as desired, provided the two terminal pads are enclosed at least at their opposite peripheries.

Although it is desired that the equipotential members are not contiguous with the terminal pads (i.e., a slight gap is provided between the former and the latter), it is possible to dispose the equipotential members without a gap to the outer periphery of the terminal pad. In this instance, considerations must be given to the pattern of band of the equipotential member and to the brazing conditions, so that the brazing material will not flow to the outer periphery of the equipotential member.

To prevent the migration of the silver content of the brazing material applied to the terminal pads, it is appreciated to cover the exposed surface of the applied mass of brazing material with a metal layer, for example, a metal plating layer, for preventing oxidization or sulfurization of the silver content of the brazing material.

While the ceramic heaters of the illustrated embodiments use a printed heating portion embedded in the ceramic body, the heating resistor used according to the invention may be provided in the form of an embedded resistance wire made of tungsten, nickel, platinum or the like, or in other forms as long as the heating resistor is formed of a material which has a positive temperature coefficient. As for the position of the heating resistor in the ceramic body, it is desired that the heating resistor be located within a portion of the tubular solid electrolyte body 1 which is exposed to an exhaust gas to be monitored by the sensor.

While the present invention has been described in its preferred embodiments, it is to be understood that the invention is not limited thereto but may be otherwise embodied within the scope of the appended claims.

What is claimed is:

1. An oxygen sensor comprising:

a tubular body of solid electrolyte having an elongate bore which is closed at one end of said tubular body and open at the other end, and further having reference and measuring electrodes on inner and outer surfaces thereof, respectively;

a housing supporting said tubular body such that said outer surface thereof is exposed at said one end to exhaust gas, said housing maintaining said elongate bore in gas-tight condition with respect to said exhaust gas; and a bar-shaped heater inserted in said elongate bore in said tubular body, and comprising a heating resistor connected to an electric power source having a positive temperature coefficient, a ceramic body carrying said heating resistor so as to embed the heating resistor, and a pair of lead wires for connecting said heating resistor to an electric power source, said ceramic body having on its outer peripheral surface a pair of terminal pads connected to said heating resistor, an end portion of each of said lead wires being brazed to corresponding one of said terminal pads with a brazing material containing silver, said ceramic body further having on said outer peripheral surface a pair of equipotential members disposed outwardly of said pair of terminal pads, respectively, said equipotential members enclosing at least portions of the peripheries of the corresponding terminal pads which are opposite to each other.

2. An oxygen sensor as recited in claim 1, wherein each of said equipotential members has a pattern of band enclosing said portions of said terminal pads, a width of said band being not less than 0.1 mm.

3. An oxygen sensor as recited in claim 1, wherein each of said equipotential members has a pattern of band enclosing said portions of said terminal pads, said pattern of band being spaced from the outer periphery of the corresponding terminal pad.

4. An oxygen sensor as recited in claim 3, wherein an area of a space between said pattern of band and the corresponding terminal pad being not more than one half of an surface area of said corresponding terminal pad.

5. An oxygen sensor as recited in claim 1, wherein said positive temperature coefficient is not less than 0.3%/° C.

* * * * *